(12) United States Patent
Khiyami

(10) Patent No.: US 8,691,521 B1
(45) Date of Patent: Apr. 8, 2014

(54) BIOLOGICAL MATERIAL EXCAVATOR AND DISPENSER APPARATUS AND METHOD OF USING THE SAME

(71) Applicant: Mohammad Ahmed Khiyami, Riyadh (SA)

(72) Inventor: Mohammad Ahmed Khiyami, Riyadh (SA)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 13/762,635

(22) Filed: Feb. 8, 2013

(51) Int. Cl.
  *C12Q 1/24* (2006.01)
  *B01L 99/00* (2010.01)

(52) U.S. Cl.
  USPC .......................................... 435/30; 422/500

(58) Field of Classification Search
  None
  See application file for complete search history.

(56) References Cited

PUBLICATIONS

Granger, B.L. 1997. A glass bead method for picking bacterial colonies. Technical Tips Online, vol. 2, pp. 138-139.*

* cited by examiner

*Primary Examiner* — John S Brusca
*Assistant Examiner* — Sharon M Papciak
(74) *Attorney, Agent, or Firm* — Geeta Kadambi Riddhi IP LLC

(57) ABSTRACT

A novel biological material excavator apparatus is described in the current invention. The apparatus is made up of a double walled tubular structure to house either a single tip or multiple tips to pick/excavate the biological material growing in agar plated petri dishes. The unique feature of this apparatus is a local ultra violet light source is present inside the apparatus to perform irradiation on site. This provides double sterilization of the apparatus as well as the tip that is being used for transferring biological material from one source to another source. The apparatus is double walled to prevent the user from being exposed to ultra violet rays while the irradiation step is being performed.

15 Claims, 5 Drawing Sheets

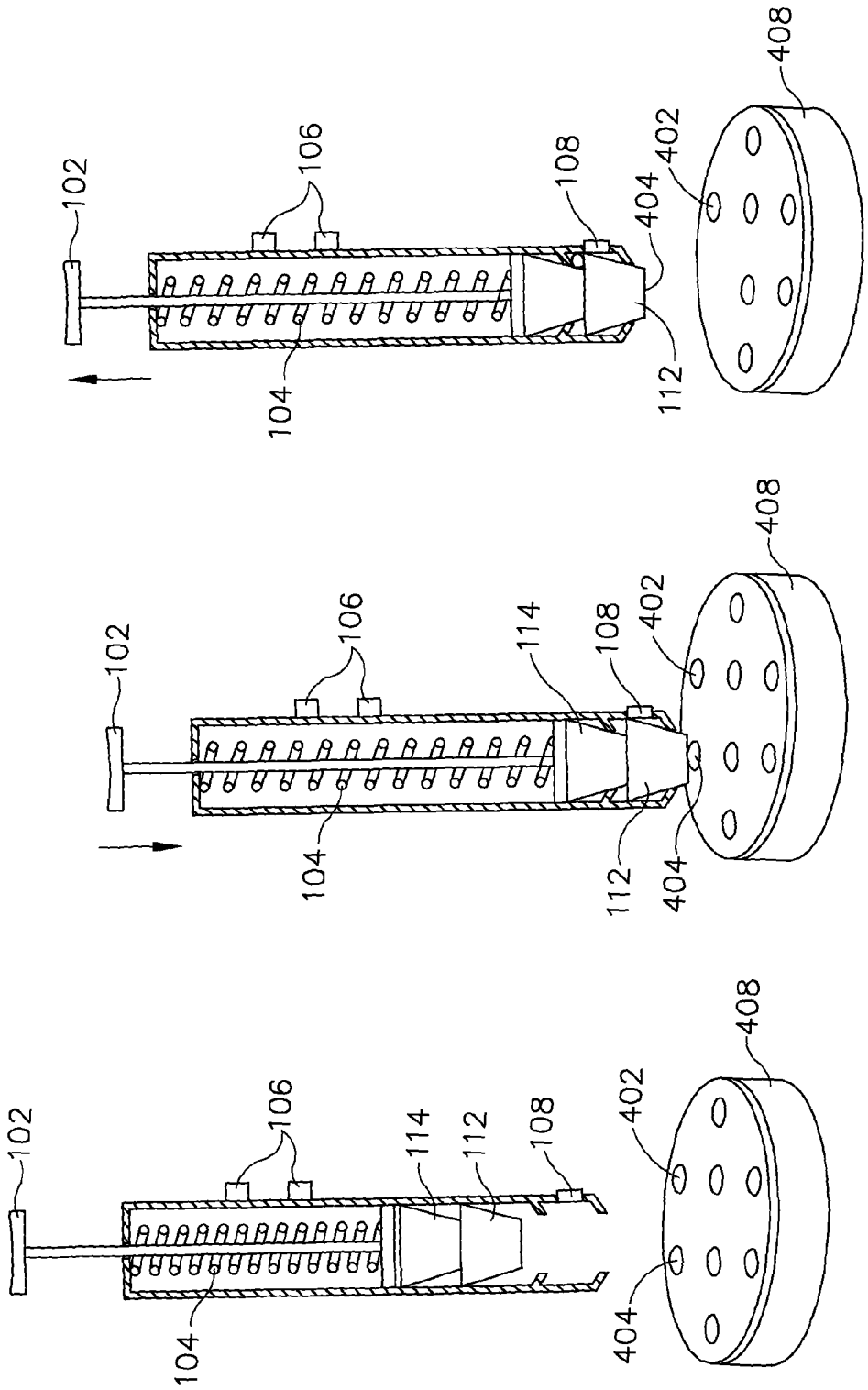

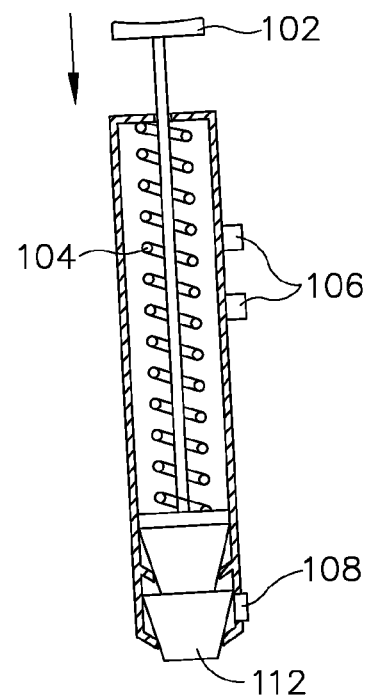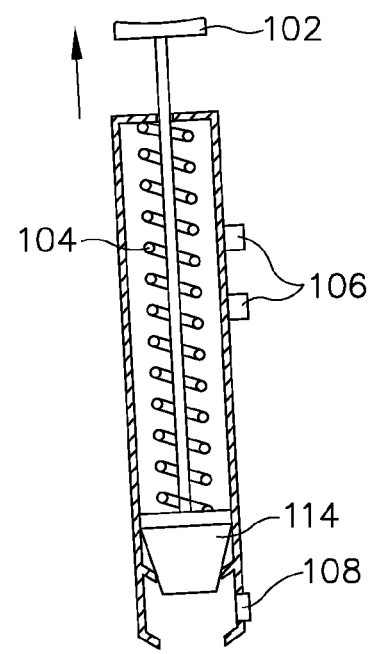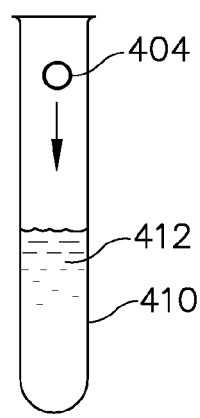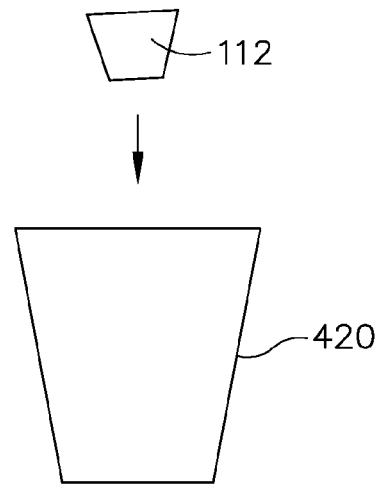
FIG.4D          FIG.4E

BIOLOGICAL MATERIAL EXCAVATOR AND DISPENSER APPARATUS AND METHOD OF USING THE SAME

FIELD OF TECHNOLOGY

This disclosure generally relates to an apparatus to excavate and dispense biological material and method of using the apparatus for excavating/picking and dispensing the biological material.

BACKGROUND

Currently forceps and/or cork borers are used to cut fungal mycelium from petri dish. Some scientist use ring picker as well. These tools need to be sterilized before usage. These tools have to be dipped in ethanol, placed in Bunsen burner flame briefly to allow ethanol to burn off. This type of sterilization is necessary to prevent cross contamination among the samples. The sterilization steps need to be followed after each sample, which is unsuitable because the forceps and cork borer might not sterilize sufficiently, or forceps and cork borer might over heat and kill the fungal mycelium. The process also can be hazardous for inexpert microbiologist when ethanol and Bunsen burner flame are not in a safe distance.

There is a need to provide a safer and sterilized mechanism for scientist to work while performing microorganism related work.

SUMMARY

The invention discloses a novel biological material excavator as an apparatus for excavating/picking the biological material in a sterile manner from the first location and dispensing it to a second location with ease. The ultra violet (UV)-C sterilization and/or decontamination of the tips in the apparatus is done just before using to make sure there is no chance for either cross contamination or contamination due to storage.

In another embodiment, the apparatus has a double walled tubular structure comprising of an inner wall and an outer wall. The outer wall may be coated with UV light protective coating. In one embodiment, the tubular structure may host a solitary single use tip or a multiple single use tips. In another embodiment, a UV light may be housed on the inner wall of the tubular structure.

In one embodiment, the apparatus may have a handle, a spring structure and a flat surface that may dispense the tip. In another embodiment, the dispenser structure has a handle to lower the dispenser, a spring like structure for ease of use to hold and compress the tips. In another embodiment, it may also have a flat surface that comes in contact with the tip directly.

The outer walls, in another embodiment, may have an on and off switch to operate the UV light embedded inside the tubular structure. The tips may be sterilized before and after the loading into the tubular structure.

In one embodiment, a method of using the sterile tip to excavate the biological material grown on a flat surface from one destination to another without contaminating while excavating or transferring is disclosed. In another embodiment, sterilizing the tip just before using for using for excavation of biological material by a biological material excavator (also cited as "apparatus" interchangeably throughout the specification for ease of use) is shown. In another embodiment, excavation of biological material without cross contaminating is described.

The novel apparatus and method of using the apparatus, disclosed herein, may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which:

FIGS. 4A, 4B and 4C shows the method of excavating the biological material using the biological material excavator is shown.

FIGS. 4D and 4E shows dispensing the excavated biological material to another destination and discarding the used tip.

Other features of the present embodiments will be apparent from the accompanying figures, tables and from the detailed description that follows.

DETAILED DESCRIPTION

Several embodiments for a novel biological material excavator (apparatus) are described. Although the present embodiments have been described with reference to specific example embodiments, it will be evident that various modifications and changes may be made to these embodiments without departing from the broader spirit and scope of the various embodiments.

Figure 1:
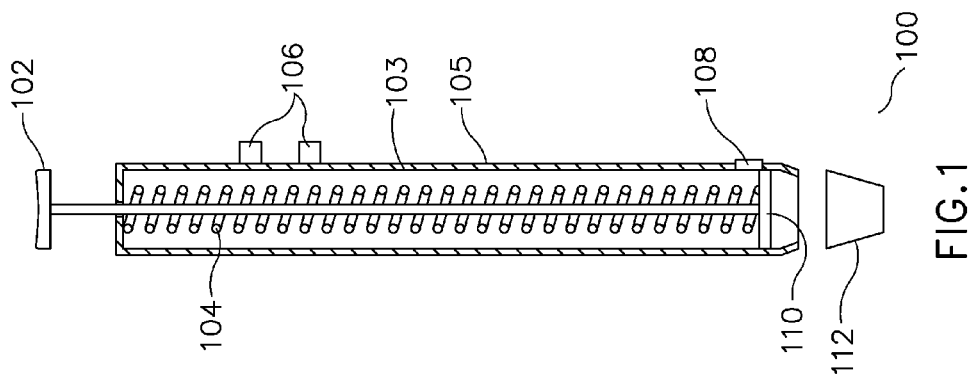
FIG. 1 shows a biological material excavator as a single use tip dispenser apparatus.

FIG. 1 shows a biological material excavator 100 apparatus as a single use tip dispenser. The tubular structure has two walls. First wall 103 is the inner wall and 105 is the outer wall. The outer wall 105 is UV resistant so that the user is protected from UV rays. The inner wall may be made up of UV protected material such as ceramic, aluminum and synthetic material. The handle 102 is flat so that the user can use their thumb to lower it easily. A flat surface 110 is at the end of the handle and comes in contact with the tip 112. It helps to lower the tip and expunge the tip 112 after use. The spring 104 is in the middle and connects the handle 102 and the flat surface 110. There are a on and off switch 106 for UV light that is housed inside the tubular structure at the lower end near the flat surface 110. The length of the apparatus may be 12-13 cm so that it makes it easier to you use with one hand. The width of the apparatus may be between 1.2 to 1.8 cm's so that the user can grip it by one hand. More specifically the width may be 1.5 cm.

UV light 108 is located at the proximal end of the tubular structure and aids in sterilizing the tip 112 before it is used. The UV light may be used for a specific time such as 10-15 minutes and specific wavelength such as 265 nm. The apparatus may also be sterilized before loading the tip by using the UV light for a specific time and specific wavelength. The tips may also be autoclaved before loading it into the apparatus. This helps to double sterilize the apparatus and tip to perform sensitive and important transfers of biological material without cross contamination. This function enables the tip 112 be sterilized or re-sterilized just before use and coming in contact with a biological material. The UV light 108 may be of c-band width so that it can kill mold and mold spores as well as microbial contaminations.

The proximal end 130 of the tube structure has two lips. The first lip would hold the tube in position so that the UV sterilization takes place properly. The second lip holds the tip 112 in place when the action of picking is performed. These lips have the quality of one way entry. The user cannot introduce the used tip back into the tubular structure and hence preventing any contamination. The wire would connect the on and off switch to the UV-C lamp (wavelengths (250-270 nm, 265 is optimum)). The biological material excavator is battery operated as well as electrically operational. The apparatus may be made up of ethanol resistant material, such as aluminum, synthetic composite, and others.

The tip design may be of any size and length. Just as an example the tips made of polypropylene so that it is UV resistant and it can be autoclaved. As a preferred embodiment, the tip height may be 0.8 cm to load 12 tips each time. The broader side of the tip may have a width of 0.8 cm and the narrower side may have a width of 0.5 cm. The tip 112 on the broader side should open 0.6 cm with a depth of 0.3 cm to allow the tips to join together. The tip broader side width should be closed after the 0.3 cm depth to give the tip strength and protect the second tip from cross contamination. The narrower side of the tip side may have a width of 0.5 cm so that it is deep enough to cut the agar that in the petri dish with sufficient thickness. At the distal end there may be two tip holders. The first one if first click level holder that performs a function of holding the tip in position to get the tip irradiated by the UV light and the second click level holder helps pick up the biological material for transfer.

Figure 2:
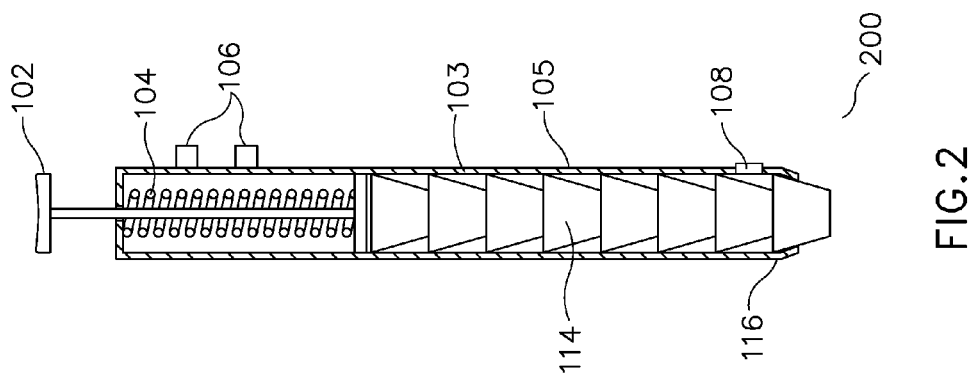
FIG. 2 shows a biological material excavator as a single multiuse tip dispenser apparatus

FIG. 2 shows multiple tip loaders with the same apparatus as described in FIG. 1. The tips 112 and 114 are stacked on top of each other. The tips may be loaded onto another tube and sterilized and loaded on to biological material excavator in a sterile environment. Multi use tips are useful so that there is no disruption in the work. Cross contamination may be avoided when the user goes in and out of the sterile area to load the tip. Also efficiency of the work is increased if there are fewer steps involved in the performance of the high throughput work. The tip 112 may be individually sterilized using conventional sterilization procedures such as autoclave etc., in the lab. The multiple tips may be enclosed in another tube like container to hold tips and the entire ensemble may be pre-sterilized before loading it on to the biological material excavator 200. This provides a unique system of double sterilization. This also eliminates the hood sterilization for the entire big surface area along with the biological material excavator 100 or 200. The same can be done for single tips. The tip may be of special shape. The tip may be broader on the top and narrower at the bottom.

Figure 3:
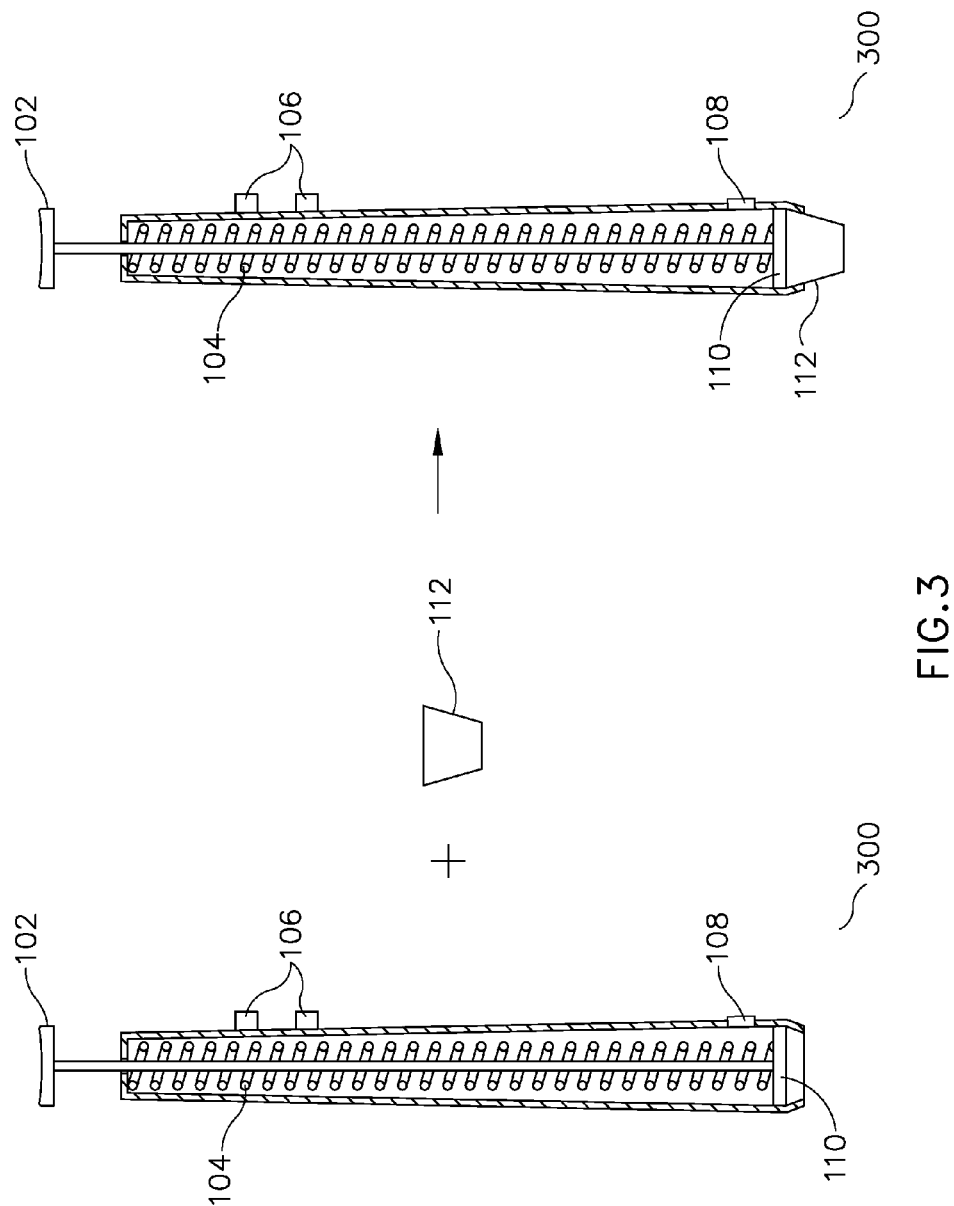
FIG. 3 shows a biological material excavator and the way to attach the tip to the biological material excavator.

FIG. 3 is another embodiment of the biological material excavator 300. This is single use apparatus. The upper part of the biological material excavator is narrower than the bottom part. A tip 112 may be obtained one a time and attached to the biological material excavator when it is needed. This is ideal for low through put use. The multi-use apparatus may be used for assembly type of functions as well. The apparatus and the tip may be autoclaved as well before use.

FIGS. 4A, 4B and 4C show the method of using the biological material excavator 100 or 200. The biological material is loaded with a single tip or multiple tips. The UV light 108 is turned on using the on switch 106. The pre-sterilized tip is sterilized again just before use using the UV light. Biological material excavator 200 is brought into close proximity of a petri dish 408. The petri dish 408 contains agar and has several colonies of biological growth 404 and 402. The tip 112 is lowered after UV sterilization to pick/excavate the colony 404 for example. Due to the shape of the tip 112 a part of agar is also picked out along with the colony of interest such as 404 in FIG. 4B. The handle 102 is pulled upwards to elevate the tip 112 that has biological material along with agar to be transferred to another petri dish or suitable container for further processing as shown in FIG. 4D. FIG. 4D shows that a tube 410 containing a media 412 is receiving the biological material excavated from petri dish 408 is transferred here. The used tip 112 is discarded in FIG. 4E after use.

Figure 5:
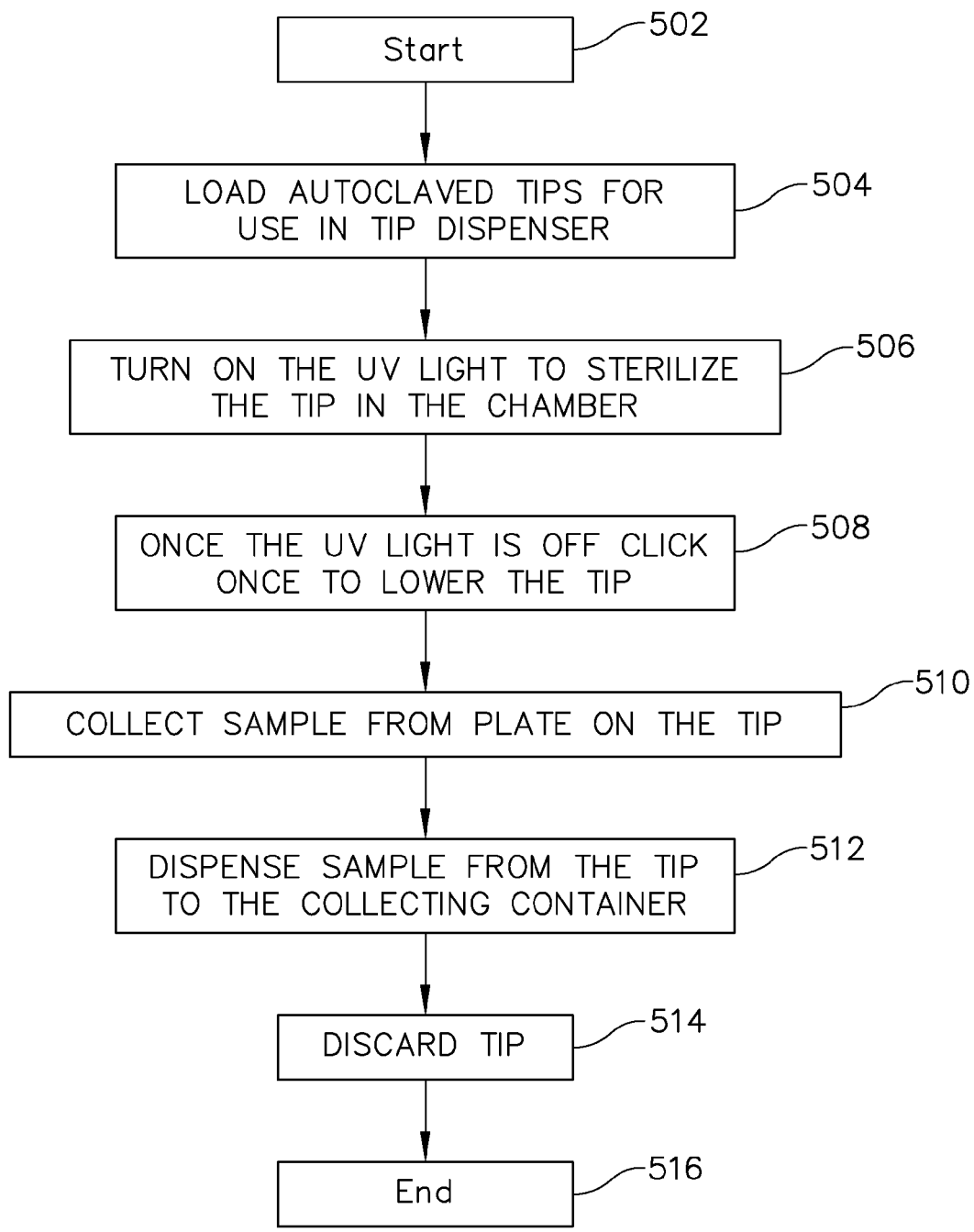
FIG. 5 shows the method of using the biological material excavator for culture work.

FIG. 5 describes the method of using the biological material excavator as a process flow. A user may sterilize the apparatus before loading the tip. A user may start 502 the process and load the autoclaved tips for use in the biological material excavator 504. The user may then turn on the UV light for a predetermined time of 10-15 minutes or 20 to 30 minutes for sterilizing the tip in the chamber 506. After the predetermined time UV light 108 using step 508 may switch off automatically and the user may click once to lower the tip 510 for picking/excavating the biological material from the petri dish 408 containing agar that is growing some sort of biological material. This action allows the first barrier in the apparatus to keep holding the tip and not allow it to be dispensed. This action also allows the tip 112 to be stable and not move when the excavation process is being performed. The sample is collected from the plate/petri dish at step 510. The collected sample is dispensed 512 from the tip 112 to a suitable receiving container such as 410 or others. The tip 112 is discarded 514 in a biological hazard waste container 420. The process then ends 516. Once the process ends the process may be restarted multiple tip holders for several other times. The apparatus may have either electrical connection to help the UV light or can be battery operated.

In addition, it will be appreciated that the various integrated container covers and methods of using the integrated container cover disclosed herein may be embodied using means for achieving cost effective material, biodegradable, light weight cheap material and useful apparatus. Accordingly, the specification and drawings are to be regarded in an illustrative rather than a restrictive sense.

What is claimed is:

1. A method to sterilely perform a biological material transfer, comprising:
   irradiating a biological material excavator using an ultra violet (UV) light for a specific time and at a specific wavelength;
   autoclaving a tip before loading it on the biological material excavator that has been irradiated to obtain a sterile tip;
   irradiating the sterile tip using the ultra violet light for the specific time and specific wavelength to obtain a sterile tip that has been doubly sterilized;
   excavating a biological material from a petri dish for transferring it to another location; and
   discarding the double sterile tip after use in a suitable container.

2. The method as in claim 1, wherein the biological material excavator is a double-walled tubular structure having an ultra violet light source built into it.

3. The method of claim 1, wherein the specific wavelength is UV-C light and the specific time is between 10-15 minutes.

4. The method of claim 1, wherein the biological material is a colony of microorganism grown on an agar plate.

5. The method of claim 1, wherein the tip has a specific dimension to fit into the tube structure of the biological material excavator.

6. The sterile method of claim 1, wherein another location is at least a test tube and petri dish.

7. A biological material excavator, comprising;
   a tubular structure having a double wall to house a tip, wherein the tip is at least one of a single tip and multiple tips, wherein the tubular wall has an inner wall and an outer wall;
   an ultra violet light source having a specific wavelength to sterilize the inner wall after being switched on a specific time;
   a handle to move the tip up and/or down of the tip; and
   the tip having a broad end and a narrow end, wherein the narrow end is used to excavate the biological material from a petri dish; and
   the broad end is used for expunging the tip from the biological material excavator.

8. The biological material excavator of claim 7, wherein the specific wavelength is UV-C light and the specific time is between 10-15 minutes.

9. The biological material excavator of claim 7, wherein inner wall is made of UV protected material at least one of a ceramic, aluminum and synthetic material.

10. The biological material excavator of claim 7, further comprising;
    a dual lip at the proximal end of the tip holder having a first click position and second click position, wherein the first click position to get the tip irradiated by the UV light and the second click position helps pick up the biological material for transfer.

11. A method to transfer biological material, comprising:
    growing a colony of biological material in a first location such as a petri dish;
    using a biological material excavator to remove the colony of biological material from the first location to a second location, wherein the biological material excavator is a double walled tube, having a handle to displace a tip and an ultra violet light source to sterilize the double walled tube and the tip; and
    transferring the colony of biological material from the tip to a second location.

12. The method of claim 11, further comprising:
    autoclaving the tip prior to loading it into the biological material excavator.

13. The method of claim 12, further comprising:
    irradiating the biological material excavator and the tip using ultra violet light of a specific wavelength and for a specific time.

14. The method of claim 13, wherein the specific wavelength is 265 nm and the specific time is between 10-15 minutes.

15. The method of claim 11, wherein the second location is at least one of a petri dish and test tube.

\* \* \* \* \*